US012359987B2

(12) United States Patent
Tabata et al.

(10) Patent No.: US 12,359,987 B2
(45) Date of Patent: Jul. 15, 2025

(54) CONTACT FORCE SENSOR AND DEVICE PROVIDED WITH CONTACT FORCE SENSOR

(71) Applicant: SEMITEC Corporation, Tokyo (JP)

(72) Inventors: Yutaro Tabata, Tokyo (JP); Manabu Orito, Tokyo (JP); Tadashi Matsudate, Tokyo (JP)

(73) Assignee: SEMITEC Corporation, Tokyo (JP)

( * ) Notice: Subject to any disclaimer, the term of this patent is extended or adjusted under 35 U.S.C. 154(b) by 412 days.

(21) Appl. No.: 17/626,804

(22) PCT Filed: Jun. 26, 2020

(86) PCT No.: PCT/JP2020/025254
§ 371 (c)(1),
(2) Date: Jan. 12, 2022

(87) PCT Pub. No.: WO2021/014890
PCT Pub. Date: Jan. 28, 2021

(65) Prior Publication Data
US 2022/0291059 A1 Sep. 15, 2022

(30) Foreign Application Priority Data
Jul. 24, 2019 (JP) .................................. 2019-136037

(51) Int. Cl.
*G01L 1/18* (2006.01)
*A61B 18/00* (2006.01)
(Continued)

(52) U.S. Cl.
CPC ................ *G01L 1/18* (2013.01); *G01L 5/162* (2013.01); *A61B 2018/00577* (2013.01);
(Continued)

(58) Field of Classification Search
CPC ....... G01L 1/18; G01L 5/162; A61B 18/1492; A61B 2018/00577; A61B 2018/00875; A61B 2090/064
See application file for complete search history.

(56) References Cited

U.S. PATENT DOCUMENTS 3,838,379 A * 9/1974 Gieles ................. G01L 19/0084
338/42
4,448,083 A * 5/1984 Hayashi ................ G01L 5/1627
73/862.042
(Continued)

FOREIGN PATENT DOCUMENTS

CN 102166136 8/2011
CN 104919292 9/2015
(Continued)

OTHER PUBLICATIONS

"International Search Report (Form PCT/ISA/210) of PCT/JP2020/025254", mailed on Jul. 21, 2020, with English translation thereof, pp. 1-4.
(Continued)

*Primary Examiner* — Ryan D Walsh
(74) *Attorney, Agent, or Firm* — JCIPRNET

(57) ABSTRACT

Provided are: a contact force sensor which has high accuracy and sensitivity and is capable of ensuring strength; and a device provided with the contact force sensor. The present invention comprises: a sensor body (2) manufactured by processing a semiconductor material, wherein the sensor body (2) is provided with: a ring-shaped portion (21); a central portion (22) formed substantially in the center of the ring-shaped portion (21); a spoke portion (23) connected to the ring-shaped portion (21) from the central portion (22) toward the outside; and stress-electricity conversion elements (5) which are disposed at positions facing each other
(Continued)

on the front side and the back side of the spoke portion (23), and convert the displacement of the spoke portion (23) into an electric signal.

22 Claims, 10 Drawing Sheets

(51) Int. Cl.
*A61B 18/14* (2006.01)
*A61B 90/00* (2016.01)
*G01L 5/162* (2020.01)

(52) U.S. Cl.
CPC . *A61B 2018/00875* (2013.01); *A61B 18/1492* (2013.01); *A61B 2090/064* (2016.02)

(56) References Cited

U.S. PATENT DOCUMENTS

| | | | | |
|---|---|---|---|---|
| 4,921,396 | A * | 5/1990 | Asakawa | B25J 15/00 403/291 |
| 4,969,366 | A * | 11/1990 | Okada | G01L 1/18 73/777 |
| 9,677,955 | B2 * | 6/2017 | Matsudate | A61B 18/1492 |
| 2015/0257799 | A1 * | 9/2015 | Janna | A61B 17/72 606/328 |
| 2015/0327921 | A1 * | 11/2015 | Govari | A61B 5/0538 606/41 |
| 2016/0334288 | A1 * | 11/2016 | Berme | G01L 5/162 |
| 2019/0346329 | A1 * | 11/2019 | Suzuki | G01L 5/0042 |
| 2020/0370978 | A1 * | 11/2020 | Yokoyama | G01L 3/108 |
| 2022/0276110 | A1 * | 9/2022 | Matsudate | G01L 19/147 |

FOREIGN PATENT DOCUMENTS

| | | |
|---|---|---|
| CN | 109959473 | 7/2019 |
| JP | S6130878 | 7/1986 |
| JP | H09329516 | 12/1997 |
| JP | H11183287 | 7/1999 |
| JP | 2007170830 | 7/2007 |
| JP | 5697186 | 4/2015 |
| JP | 5913812 | 4/2016 |

OTHER PUBLICATIONS

Office Action of China Counterpart Application, with English translation thereof, issued on Jun. 17, 2024, pp. 1-23.
"The Second Office Action of China Counterpart Application", with English translation thereof, issued on Dec. 16, 2024, pp. 1-21.

* cited by examiner

CONTACT FORCE SENSOR AND DEVICE PROVIDED WITH CONTACT FORCE SENSOR

CROSS-REFERENCE TO RELATED APPLICATION

This application is a 371 application of the International PCT application serial no. PCT/JP2020/025254, filed on Jun. 26, 2020, which claims the priority benefits of Japan Patent Application No. 2019-136037, filed on Jul. 24, 2019. The entirety of each of the above-mentioned patent applications is hereby incorporated by reference herein and made a part of this specification.

TECHNICAL FIELD

The present invention relates to a contact force sensor and a device provided with the contact force sensor, which are suitable for use in the field of medical instruments.

RELATED ART

Conventionally, for example, an ablation catheter has been used for the treatment of atrial arrhythmia. In the ablation treatment using this ablation catheter, an electrode of the ablation catheter is brought into contact with an abnormal portion on the inner wall of a heart, and a high-frequency current is applied to cauterize the abnormal portion.

Therefore, a catheter has been known in which a contact force sensor that detects a contact force of the electrode is arranged at a front end of the catheter (see Patent literatures 1 and 2).

However, the catheter shown in Patent literature 1 has a configuration in which a sensor (strain gauge) is attached to an arm by an adhesive, and there are problems that variation in the attachment position of the sensor tends to occur, and it is difficult to adjust the output of the sensor. In addition, there is also a problem that the sensitivity of the sensor decreases due to the attachment configuration in which the adhesive is interposed.

In addition, the catheter shown in Patent literature 2 has a configuration in which a first sensor constitution body and a second sensor constitution body are joined by soldering in a way of sandwiching a sensor and a lead wire, and thus there is a possibility that positions of the first sensor constitution body and the second sensor constitution body may be misaligned. Additionally, because the joining is performed by soldering, there is a problem that the strength is not sufficient.

CITATION LIST

Patent Literature

Patent Literature 1: Japanese Patent No. 5913812
Patent Literature 2: Japanese Patent No. 5697186

SUMMARY OF INVENTION

Technical Problem

The present invention has been made in view of the above problems, and an objective of the present invention is to provide a contact force sensor which has high accuracy and sensitivity and is capable of ensuring strength, and a device provided with the contact force sensor.

Solution to Problem

An embodiment of the present invention is a contact force sensor including a sensor body manufactured by processing a semiconductor material, wherein the sensor body is provided with: a ring-shaped portion; a central portion formed substantially in a center of the ring-shaped portion; a spoke portion coupled to the ring-shaped portion from the central portion toward outside; and stress-electricity conversion elements which are disposed at positions facing each other on a front side and a back side of the spoke portion, and convert displacement of the spoke portion into an electric signal.

According to the configuration, the accuracy and sensitivity can be made high, and the strength can be ensured.

In addition, a device provided with a contact force sensor is provided with the contact force sensor.

The contact force sensor is suitably used in devices such as medical instruments and the like, but is not limited hereto. The contact force sensor can be applied to various devices that are required to be miniaturized, and the device to which the contact force sensor is specifically applied is not limited.

Effects of Invention

According to the embodiment of the present invention, it is possible to provide a contact force sensor which has high accuracy and sensitivity and is capable of ensuring strength, and a device provided with the contact force sensor.

DESCRIPTION OF EMBODIMENTS

Figure 1:
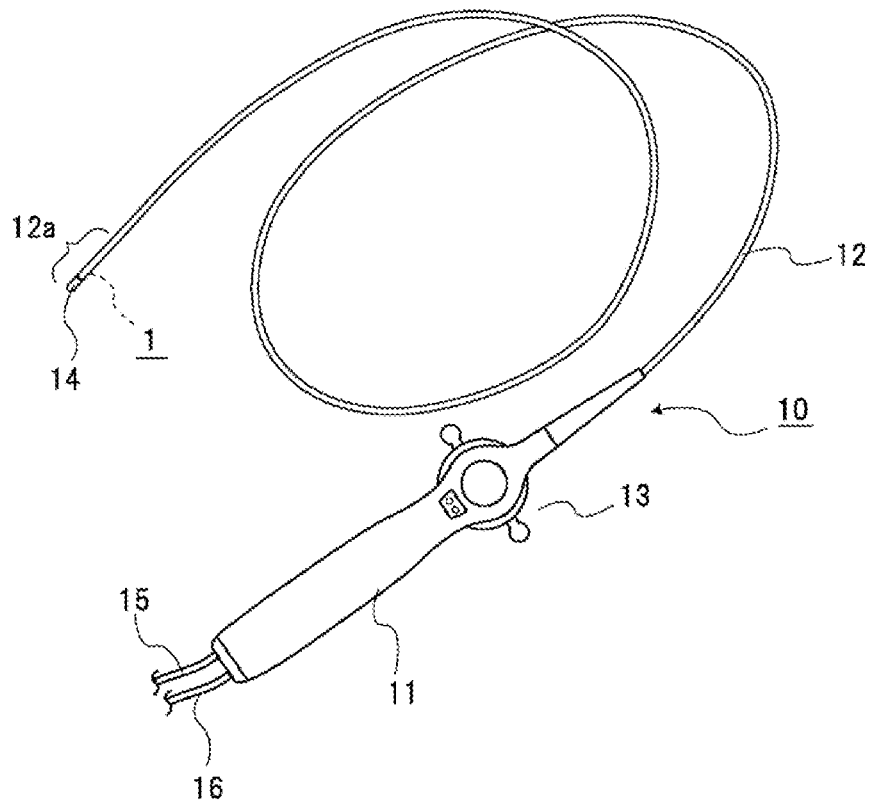
FIG. 1 includes a plan view showing a catheter to which a contact force sensor according to an embodiment of the present invention is applied, and a cross-sectional view for explaining an outline at a front end of the catheter.
Figure 1:
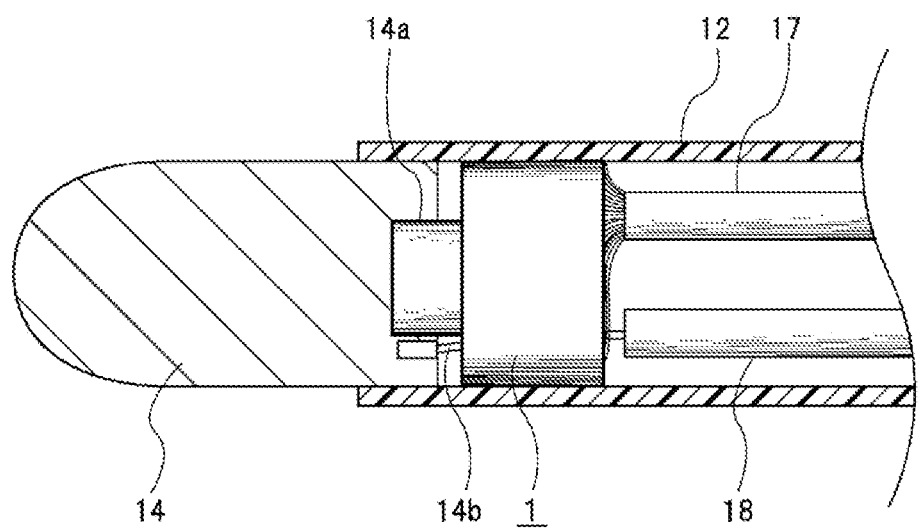
Figure 2:
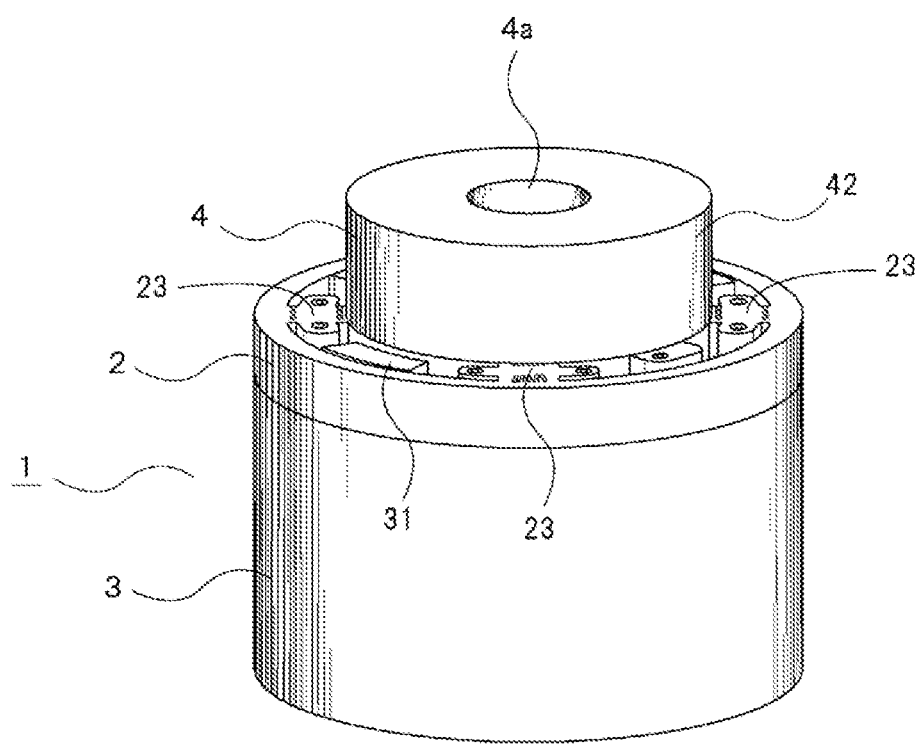
FIG. 2 is a perspective view showing the contact force sensor.
Figure 3:
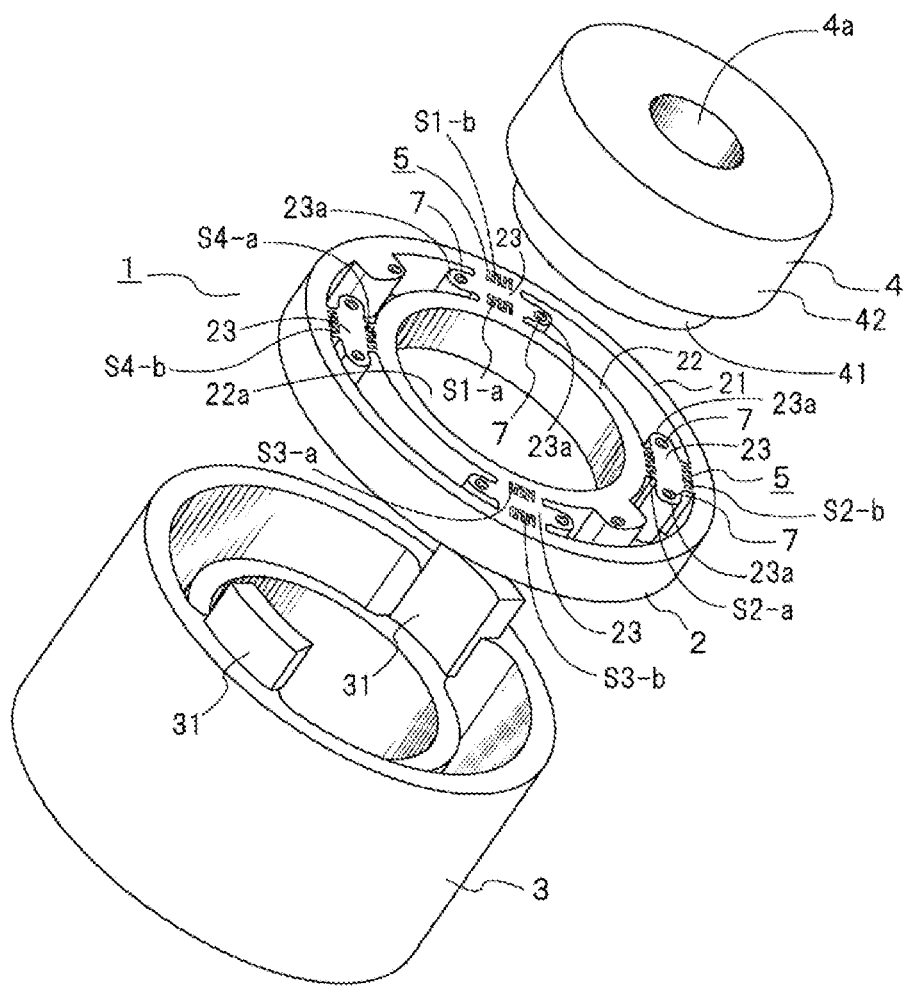
FIG. 3 is a perspective view showing the contact force sensor in an exploded manner.
Figure 4:
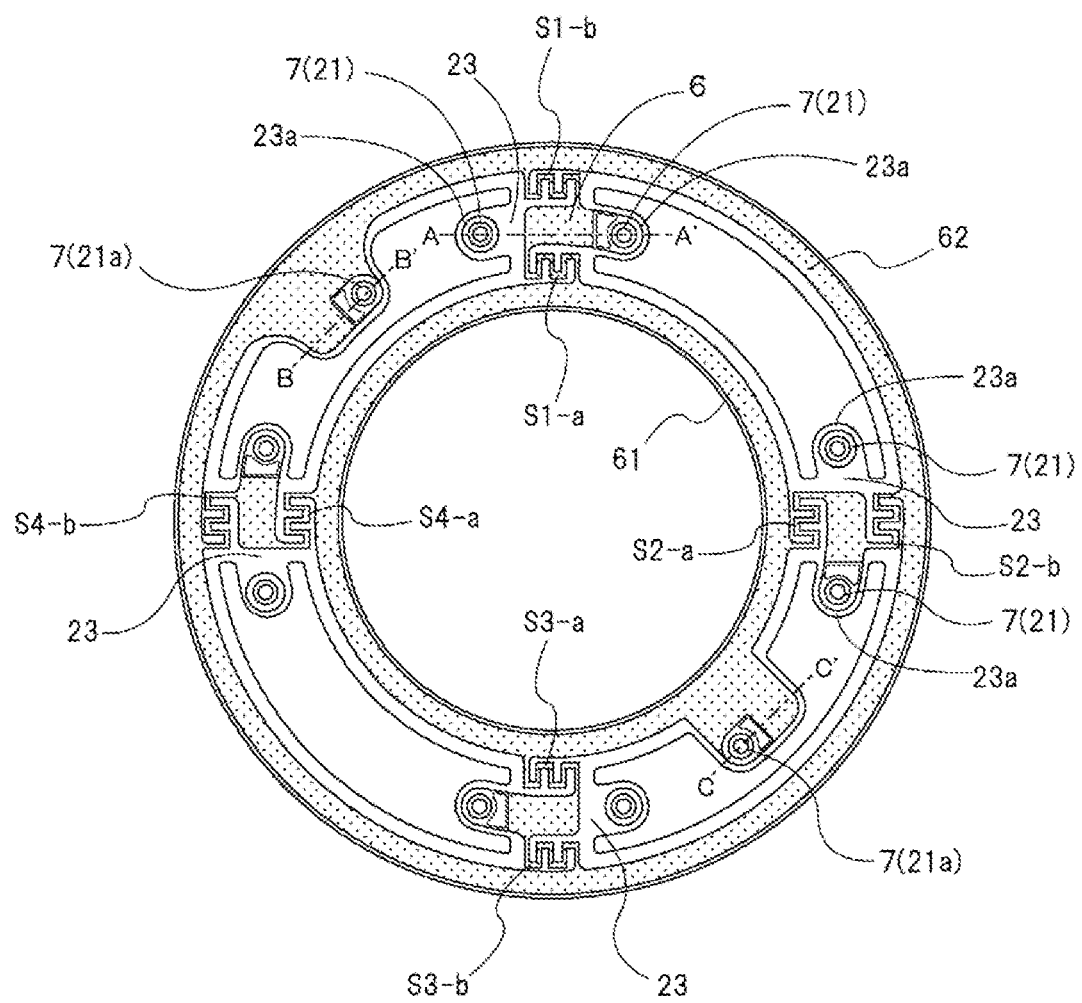
FIG. 4 is a plan view showing the front side of the sensor body in the contact force sensor.
Figure 5:
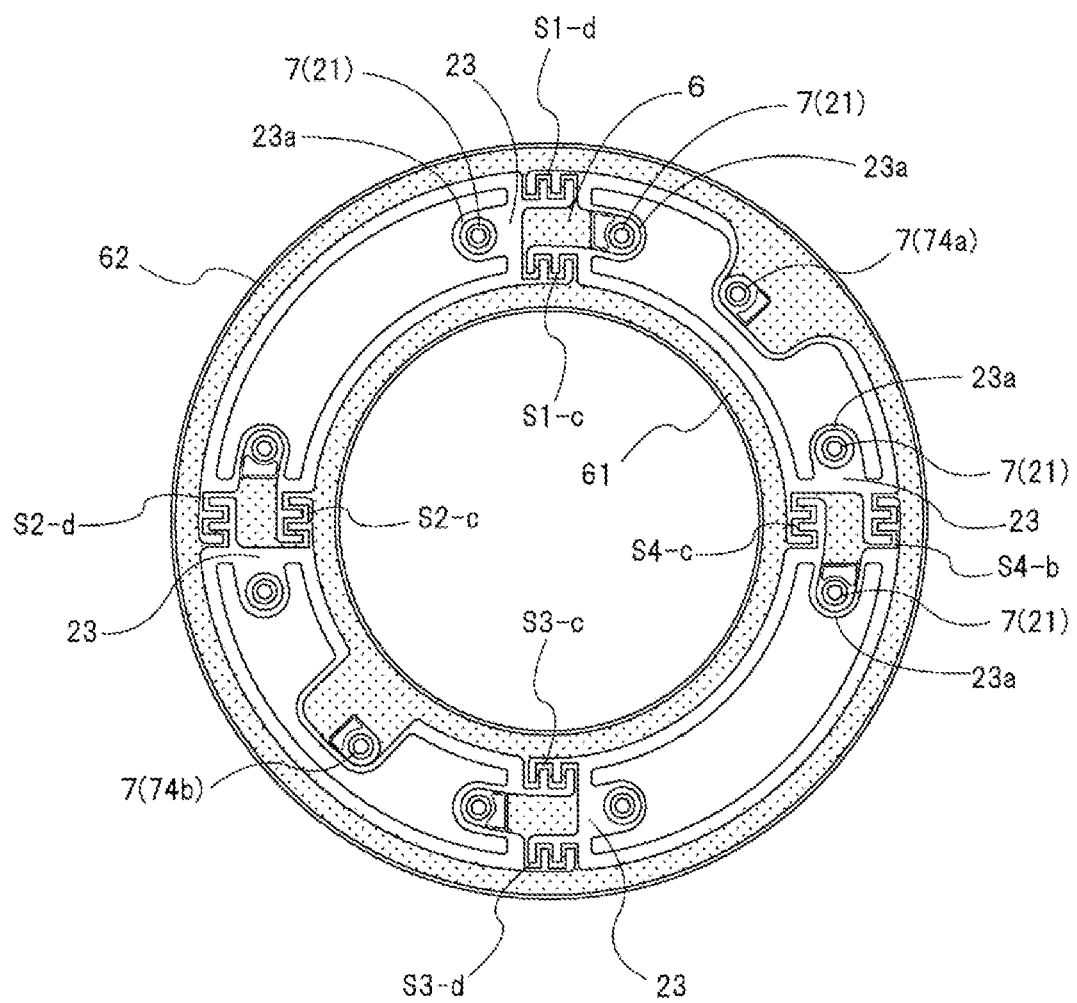
FIG. 5 is a plan view showing the back side of the sensor body in the contact force sensor.
Figure 6:
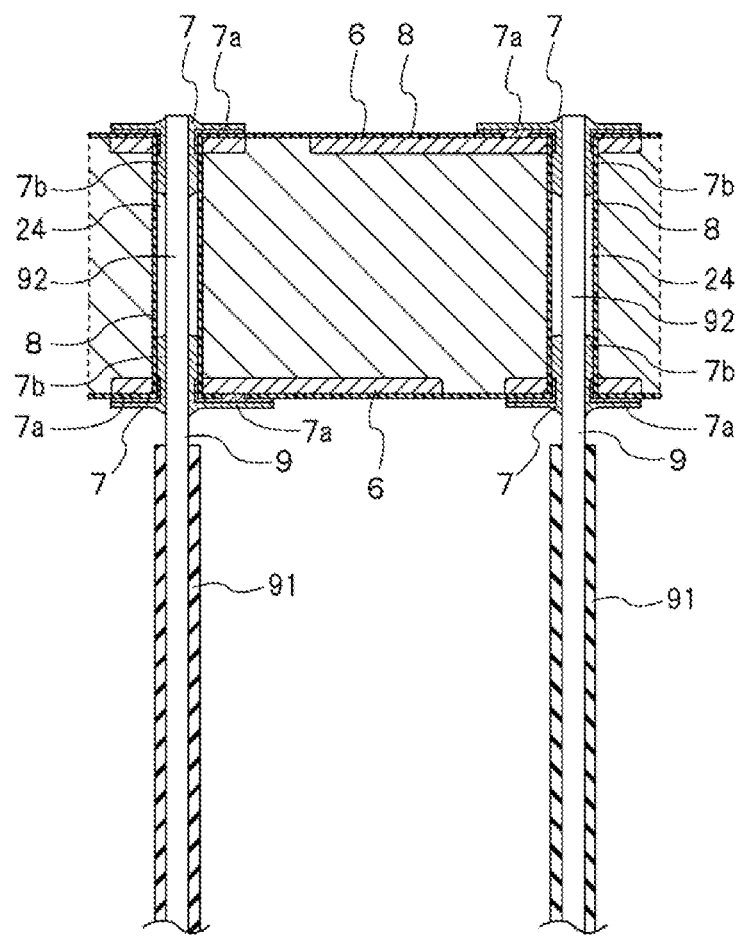
FIG. 6 is a cross-sectional view taken along an A-A' line in FIG. 4.
Figure 7:
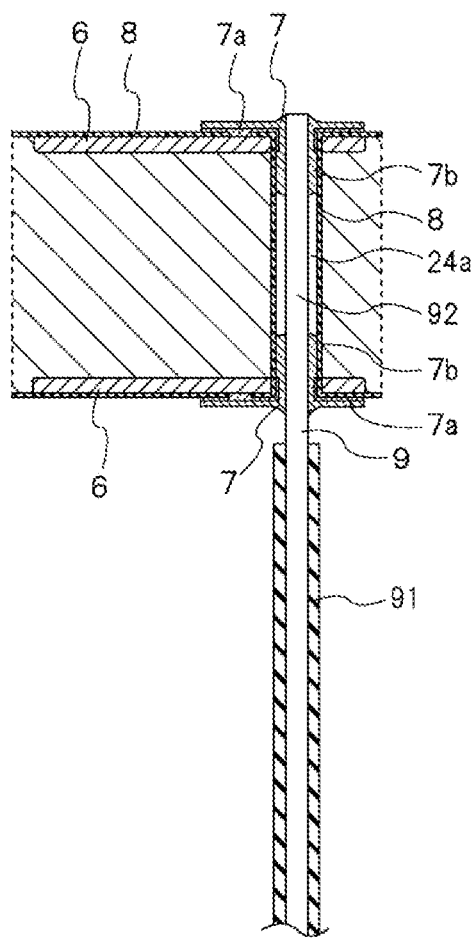
FIG. 7 is a cross-sectional view taken along a B-B' line in FIG. 4.
Figure 8:
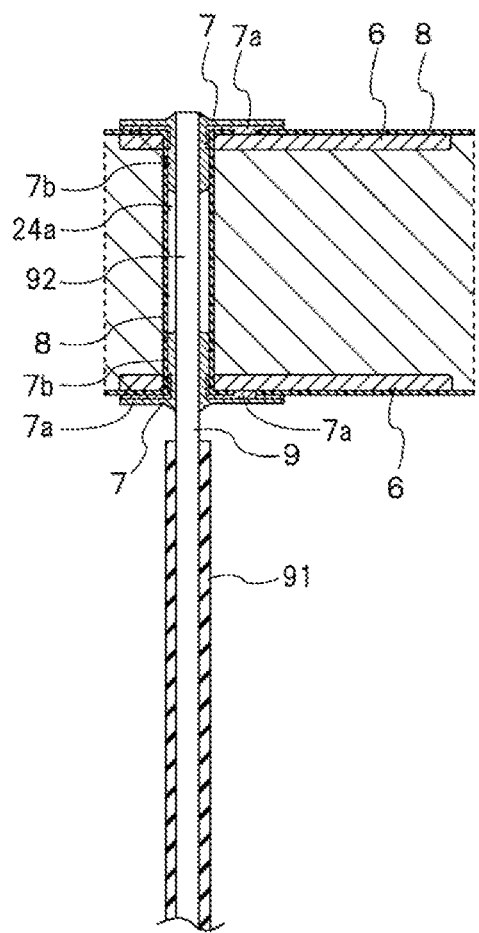
FIG. 8 is a cross-sectional view taken along a C-C' line in FIG. 4.
Figure 9:
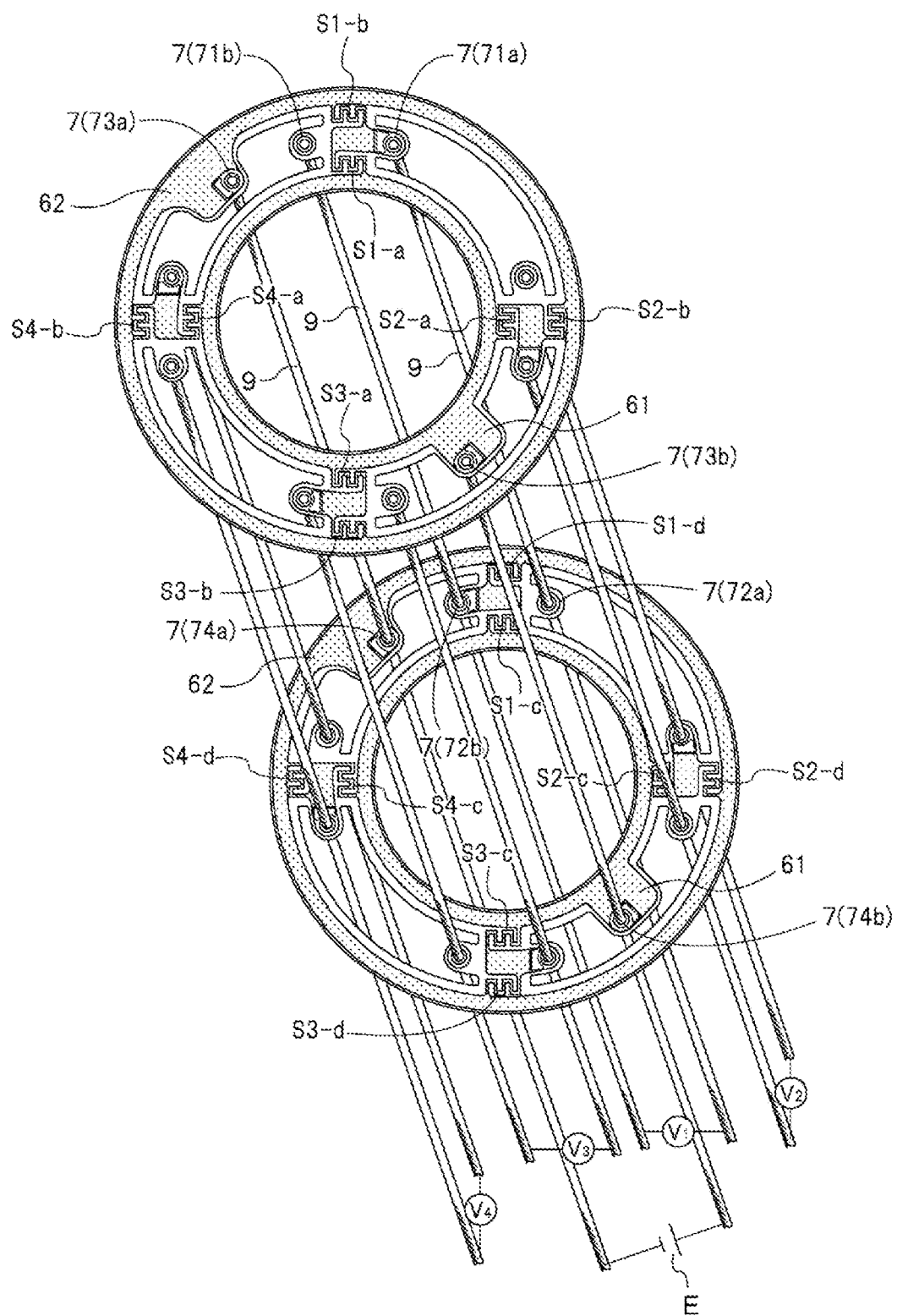
FIG. 9 is a substantive explanatory diagram for explaining a wire connection relationship of the sensor body in the contact force sensor.
Figure 10:
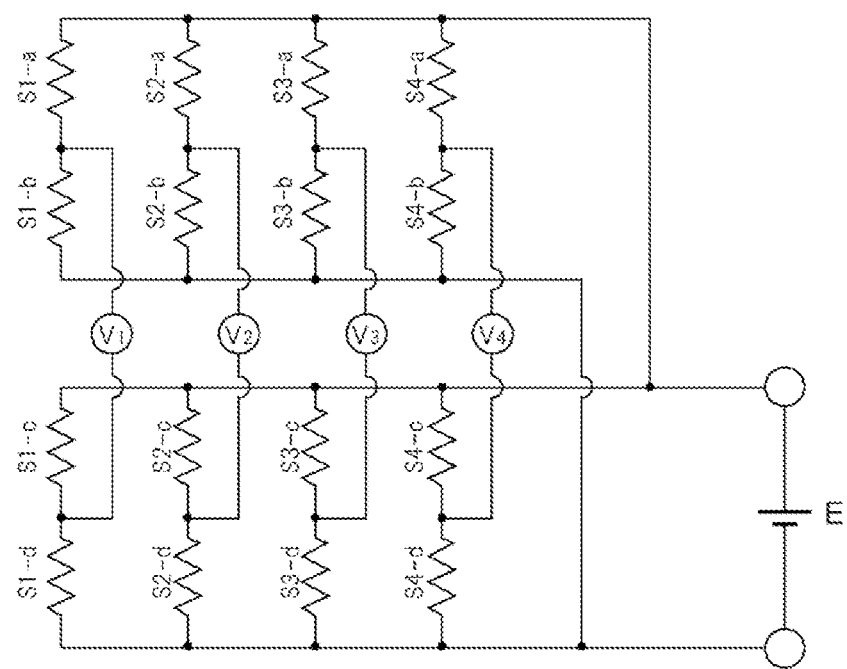
FIG. 10 is a bridge circuit diagram showing a connection state of stress-electricity conversion elements.

Hereinafter, a contact force sensor according to an embodiment of the present invention is described with reference to FIGS. 1 to 10. FIG. 1 includes a plan view showing an outline of a catheter to which a contact force sensor is applied, and a cross-sectional view for explaining a front end of the catheter; FIG. 2 is a perspective view showing the contact force sensor; and FIG. 3 is a perspective view showing the contact force sensor in an exploded manner. FIG. 4 is a plan view showing the front side of a sensor body in the contact force sensor, and FIG. 5 is a plan view showing the back side of the sensor body. FIG. 6 is a cross-sectional view taken along an A-A' line in FIG. 4; FIG. 7 is a cross-sectional view taken along a B-B' line in FIG. 4; and FIG. 8 is a cross-sectional view taken along a C-C' line in FIG. 4. In addition, FIG. 9 is a substantive explanatory diagram for explaining a wire connection relationship of the sensor body in the contact force sensor, and FIG. 10 is a bridge circuit diagram showing a connection state of stress-electricity conversion elements. It should be noted that in each drawing, the scale of each member is appropriately changed in order to make each member recognizable. In addition, sometimes the front end side of the catheter may be referred to as the front side, and the rear end side may be referred to as the back side.

The contact force sensor of the embodiment illustrates a contact force sensor which is applied to medical treatment in a manner of being incorporated into an ablation catheter and measuring a contact force of an electrode of the ablation catheter to an abnormal portion on the inner wall of a heart in order for ablation treatment.

As shown in FIG. 1, a catheter 10 is an ablation catheter and is provided with: a control handle 11, and a shaft 12 led out from one end side of the control handle 11. In addition, a deflection member 13 is arranged at the control handle 11, and a front-end electrode 14 is arranged at a front end 12a of the shaft 12. Furthermore, a contact force sensor 1 is disposed inside the shaft 12 at the front end 12a of the shaft 12.

The deflection member 13 arranged at the control handle 11 is a member for operating the front end 12a of the shaft 12 to deflect and move, and makes the front end 12a of the shaft 12 deflect and move in two directions by pulling an operation wire (not shown) disposed inside the shaft 12.

From the rear of the control handle 11, a cable 15 connected to a high-frequency generator or a controller, and an irrigation tube 16 connected to a fluid source are led out. The high-frequency generator is connected to the front-end electrode 14 and supplies high-frequency energy to the front-end electrode 14. In addition, the controller has functions for controlling an electrical output signal or input signal to control the state of high-frequency energization to the front-end electrode 14, and receiving an output signal from the contact force sensor 1 to measure the contact force.

The shaft 12 has an elongated shape, has a lumen formed therein, and has appropriate rigidity and flexibility. In addition, lead wire insertion tubes 17 and 18 having a hollow shape are disposed along a longitudinal direction inside the lumen. An outer diameter dimension of the shaft 12 is 8 Fr or less, and a length dimension of the shaft 12 is formed to be 900 mm to 1100 mm.

In addition, the front-end electrode 14 is formed in a cannonball shape and is fixed to the front end 12a of the shaft 12. The front-end electrode 14 has a recess 14a having a cylindrical shape on the back side. The contact force sensor 1 is coupled to the recess 14a. Furthermore, an electrode lead wire 14b is connected to the back side of the front-end electrode 14. The electrode lead wire 14b is inserted into the lead wire insertion tube 18 and is connected to the high-frequency generator. That is, the front-end electrode 14 is electrically connected to the high-frequency generator, and high-frequency energy is supplied from the high-frequency generator to the front-end electrode 14.

An outer diameter dimension of the front-end electrode 14 is preferably substantially the same as the outer diameter dimension of the shaft 12, and is formed to be 8 Fr or less. In addition, as a material constituting the front-end electrode 14, for example, a metal material having good thermal conductivity such as platinum, gold, stainless steel, or a titanium alloy can be used. Moreover, a flow path (not shown) for sending a fluid such as physiological saline conveyed from the irrigation tube 16 to the outside is formed at the front-end electrode 14.

In this catheter 10, when the front-end electrode 14 comes into contact with the abnormal portion on the inner wall of a heart, a stress applied to the front-end electrode 14 by the contact is transmitted to the contact force sensor 1, and the contact force can be measured. Next, the contact force sensor 1 is described in detail with reference to FIGS. 2 and 3.

The contact force sensor 1 is manufactured from a silicon semiconductor material by micro electro mechanical system (MEMS) technology using a semiconductor processing process. The contact force sensor 1 is provided with: a sensor body 2, a holding body 3, and a contact force transmission body 4.

The sensor body 2 has a substantially short cylindrical shape as a whole, and includes: a ring-shaped portion 21; a central portion 22 formed substantially in the center of the ring-shaped portion 21; a spoke portion 23 coupled to the ring-shaped portion 21 from the central portion 22 toward the outside; and a stress-electricity conversion element 5 which is disposed and formed in the spoke portion 23.

The ring-shaped portion 21 is a cylindrical part that forms the outer shell of the sensor body 2. On the inner side of the ring-shaped portion 21 and substantially in the center, the central portion 22 being ring-shaped and having a diameter smaller than that of the ring-shaped portion 21 is formed. In other words, an opening 22a is formed in the central portion 22 in a front-back direction.

The spoke portion 23 is formed from the outer wall side of the central portion 22 to the inner wall side of the ring-shaped portion 21 in a radial direction. In addition, bulge portions 23a are formed on two sides of an intermediate part of the spoke portion 23, specifically, on two sides in a circumferential direction intersecting the radial direction. A plurality of the spoke portions 23 are formed, and specifically, four above-described spoke portions 23 are respectively formed radially at intervals of 90 degrees on a circumference centering on the central portion 22.

With reference to and as shown in FIGS. 4 and 5, the stress-electricity conversion elements 5 are formed on both the front side surface and the back side surface of the spoke portion 23. For the sake of explanation, the stress-electricity conversion elements 5 are shown by solid lines, but in reality, the stress-electricity conversion elements 5 are formed in a way of being integrally built in the sensor body 2. The stress-electricity conversion elements 5 convert the displacement of the spoke portion 23 into an electric signal, and are piezo resistance elements having a function of a strain gauge in which an electric resistance changes due to the displacement of the spoke portion 23 when a strain is applied.

On one surface side, specifically, on the front side of the spoke portion 23, these piezo resistance elements (S1-*a*, S1-*b*), (S2-*a*, S2-*b*), (S3-*a*, S3-*b*), and (S4-*a*, S4-*b*) are respectively arranged on the center side and the outer periphery side of each spoke portion 23. That is, each pair of the piezo resistance elements (S1-*a*, S1-*b*), (S2-*a*, S2-*b*), (S3-*a*, S3-*b*), and (S4-*a*, S4-*b*) is respectively arranged at each spoke portion 23. In addition, electrodes 7 are formed at the bulge portions 23a of the spoke portions 23 at which the piezo resistance elements (S1-a, S1-b), (S2-a, S2-b), (S3-a, S3-b), and (S4-a, S4-b) are arranged. The electrodes 7 are electrically connected to the power supply side.

Furthermore, a wiring pattern 6 which is a conductive layer is formed on the front side of the spoke portion 23, an inner wiring pattern 61 having a ring shape is formed on the side closer to the inner periphery, and similarly, an outer wiring pattern 62 having a ring shape is formed on the side closer to the outer periphery.

In addition, the configuration of the spoke portion 23 on the other surface side, specifically, on the back side, is basically the same as that on the front side. Similar to the case of the front side described above, on the center side and the outer periphery side of each spoke portion 23, each pair of piezo resistance elements (S1-c, S1-d), (S2-c, S2-d), (S3-c, S3-d), and (S4-c, S4-d) is respectively arranged. In addition, the electrodes 7 are formed at the bulge portions 23a of the spoke portions 23. In addition, the wiring pattern 6 is formed in the same manner.

These stress-electricity conversion elements 5 are disposed at positions facing each other on the front side and the back side of the spoke portion 23. For example, taking the piezo resistance elements (S1-a, S1-b) on the front side and the piezo resistance elements (S1-c, S1-d) on the back side as typical examples to describe an arrangement relationship of the stress-electricity conversion elements 5, the piezo resistance elements (S1-a) and (S1-c) are disposed at positions facing each other, and the piezo resistance elements (S1-b) and (S1-d) are disposed at positions facing each other. In addition, the electrodes 7 are also disposed at positions facing each other on the front side and the back side.

In the above arrangement relationship, as shown in FIG. 4, the piezo resistance element (S1-a) and the piezo resistance element (S1-b) on the front side are connected via the wiring pattern 6, and the electrodes 7 are connected between the piezo resistance element (S1-a) and the piezo resistance element (S1-b). Furthermore, the piezo resistance element (S1-a) is connected to the inner wiring pattern 61, and the piezo resistance element (S1-b) is connected to the outer wiring pattern 62.

According to this connection relationship of the piezo resistance elements (S1-a, S1-b), (S2-a, S2-b), (S3-a, S3-b), and (S4-a, S4-b), the piezo resistance elements (S1-a, S1-b), (S2-a, S2-b), (S3-a, S3-b), and (S4-a, S4-b) are commonly connected to the inner wiring pattern 61 and the outer wiring pattern 62, and thus it is possible to reduce the number of lead wires and simplify the wiring. In addition, as shown in FIG. 5, the piezo resistance elements (S1-c, S1-d), (S2-c, S2-d), (S3-c, S3-d), and (S4-c, S4-d) on the back side also have the same connection relationship. Next, a connection configuration of the electrode and the lead wire is described with reference to FIGS. 6 to 8.

In the sensor body 2, a through hole 24 is formed from one surface side (the front side) toward the other surface side (the back side). The through hole 24 is a hole through which a lead wire 9 electrically connected to the stress-electricity conversion element 5 passes, and is formed between the electrodes 7 facing each other disposed on the front side and the back side.

Thus, as shown in FIGS. 4 and 5, in a plan view, the through holes 24 are located and formed on two sides of the respective piezo resistance elements (S1-a, S1-b) and (S1-c, S1-d), (S2-a, S2-b) and (S2-c, S2-d), (S3-a, S3-b) and (S3-c, S3-d), and (S4-a, S4-b) and (S4-c, S4-d), specifically, on two sides in the circumferential direction intersecting the radial direction. In addition, through holes 24a for the connection to a power supply line are formed facing each other in the radial direction. Specifically, a total of ten through holes 24 and 24a, namely eight through holes 24 formed on two sides of the piezo resistance elements and two through holes 24a for the connection to the power supply line, are formed.

A diameter dimension of the through hole 24 is preferably about ϕ40 μm to ϕ60 μm, and is formed to be ϕ50 μm in the embodiment.

On surfaces of the sensor body 2 on the front side and the back side, the wiring patterns 6 are formed as conductive layers by diffusion. The conductive layers are electrically connected to the stress-electricity conversion elements 5.

In addition, an insulation layer 8 is formed on the inner wall of the through hole 24, and the inner wall of the through hole 24 is coated by the insulation layer 8. Thus, the inside of the through hole 24 is in a state that an insulation property is ensured. The insulation layer 8 is also formed so as to extend to the front side and the back side of the sensor body 2. In order that the wiring pattern 6 and the lead wire 9 are electrically connected via the electrode 7, the insulation layer 8 on the front side and the back side of the sensor body 2 coats the wiring pattern 6 in a way that a part of the wiring pattern 6 is exposed as a conductive layer. Moreover, the insulation layer 8 is formed by, for example, a material of silicon dioxide, and has a thickness dimension of 1 μm to 2 μm.

In addition, on the insulation layer 8 and around the front side and the back side of the through hole 24, an electrode layer 7a is deposited by a thin film forming technique such as a sputtering method or the like. The electrode layer 7a is connected to the wiring pattern 6 at a portion where a part of the wiring pattern 6 is partially exposed, and is formed in a way of slightly extending toward the inner wall side of the through hole 24. A material for forming the electrode layer 7a may be, for example, titanium/copper (Ti/Cu), an aluminum-silicon alloy (Al—Si), titanium/tungsten (Ti/W), or the like. In the case of an electrode layer having a three-layer structure, the material may be titanium/copper/gold (Ti/Cu/Au) and the like.

The electrode 7 electrically connects the lead wire 9 to the stress-electricity conversion element 5, and the electrode 7 of the embodiment is made of a solder-plated brazing material. As the brazing material, for example, tin (Sn) (melting point: 231.1° C.), which is a metal having a low melting point, is used. In addition, nickel (Ni) is used for the base plating. Moreover, as the brazing material, indium (In) (melting point: 156.6° C.), which is a metal having a low melting point, and a general solder material can be used.

The lead wire 9 is an insulation-coated electric wire in which a conductor core wire is formed by a copper-silver alloy (Cu—Ag) wire. The lead wire 9 has high bending strength and tensile strength, and the strength can be significantly improved as compared with a general case where the conductor core wire is formed by copper (Cu). In particular, it has been known that the strength is significantly improved when the silver content is increased from 3% to 15%. The lead wire 9 has an insulation coating 91 made of perfluoro alkoxy alkane (PFA) resin which is fluororesin. A bare conductor core wire portion 92, from which the insulation coating 91 has been peeled off and removed, is introduced in a way of passing through the through hole 24 of the sensor body 2, and a front end of the conductor core wire portion 92 has a linear shape without being bent.

The conductor core wire portion 92 of the lead wire 9 is not precluded from direct contact with the electrode layer 7a, but is joined to the electrode layer 7a via a brazing material taken as the electrode 7 without directly coming into contact with the electrode layer 7a. The brazing material is joined to the electrode layer 7a and connected to the wiring pattern 6 and the stress-electricity conversion element 5. In addition, the electrode 7 enters a part of the inside of the through hole 24 to form an intrusion portion 7b. This lead wire 9 is led out toward the back side of the sensor body 2, and an end of the lead wire 9 is connected to the control handle 11. Note that, a diameter dimension of the conductor core wire portion 92 of the lead wire 9 is preferably about φ15 μm to φ30 μm, and is φ25 μm in the embodiment. Thus, a gap of about 10 μm is formed between an outer periphery of the conductor core wire portion 92 passing through the through hole 24 and the inner wall of the through hole 24.

In addition, with regard to the lead wire 9 led out from the back side of the sensor body 2, a led-out part thereof may be fixed by an adhesive such as an epoxy resin or the like.

Furthermore, an outer surface of the sensor body 2 and an outer surface of the part fixed by the adhesive are preferably insulation-coated by an insulation material having flexibility in order to ensure waterproofness, insulation properties, and softness. In this case, parylene (registered trademark) or a silicone coating material can be suitably used. Note that, a thickness dimension of the insulation coating is 2 μm to 3 μm.

When there is a high risk that component parts in an instrument used in a catheter or the like, which is a medical instrument, are exposed in a living body, it is required that the material to be used is a material with consideration of biocompatibility. At least the outer surface of the sensor body 2 is coated by parylene (registered trademark), and the insulating coating 91 is formed on the lead wire 9 by fluororesin. Additionally, the sensor body 2 is made of a silicon material. These materials are confirmed to have biocompatibility, and the safety can be ensured.

According to the above configuration, because the insulation layer 8 is formed on the inner wall of the through hole 24, the bare conductor core wire portion 92 from which the insulation coating 91 has been peeled off can pass through the through hole 24 while the insulation property is ensured. Thus, when the size of the through hole 24 is limited to have an extremely small diameter, because the insulation coating 91 is peeled off and removed, it is possible to use a thick lead wire 9 in which the conductor core wire has a great diameter correspondingly. That is, it is possible to use a thick lead wire 9 in which the core wire has a diameter close to a hole diameter of the through hole 24, and it is possible to increase tensile strength and improve reliability.

Because the conductor core wire portion 92 of the lead wire 9 can be made thick, by melting the solder-plated brazing material taken as the electrode 7 after the conductor core wire portion 92 is inserted into and passes through the through hole 24, the lead wire 9 can be joined to the electrode layer 7a, thereby facilitating the joining step.

In addition, because the electrode 7 enters the inside of the through hole 24 to form the intrusion portion 7b, a connection state of the lead wire 9 becomes reliable, and a connection deviation of the lead wire 9 can be prevented.

Furthermore, because the front end of the conductor core wire portion 92 in the lead wire 9 has a linear shape without being bent, and the electrode 7 is formed by solder plating, the amount of protrusion to one surface side of the sensor body 2 can be reduced. In addition, the amount of the brazing material subjected to solder plating can be reduced, and a stress applied to the spoke portion 23 of the sensor body 2 can be reduced.

The contact force sensor 1 is described with reference to FIGS. 2 and 3 again.

The sensor body 2 described above is attached to the holding body 3 taken as a base member by adhesion, wafer joining, or the like. In addition, the contact force transmission body 4 is attached to and arranged on the front side of the sensor body 2 by adhesion, wafer joining, or the like.

The holding body 3 holds the sensor body 2, has a substantially cylindrical shape in which a central portion is hollow, and is formed to have an outer diameter dimension substantially the same as an outer diameter dimension of the sensor body 2. In addition, a pair of claw-shaped portions 31 are formed on the front side so as to support the sensor body 2 when the sensor body 2 is coupled to the holding body 3.

The contact force transmission body 4 is a two-stage member which has an insertion hole 4a formed in the front-back direction in a central portion and includes a small diameter portion 41 and a great diameter portion 42. The contact force transmission body 4 is arranged and coupled to the sensor body 2 in a way that the small diameter portion 41 is fitted into the opening 22a of the central portion 22 of the sensor body 2, and the back side of the great diameter portion 42 is placed on the central portion 22.

In addition, the sensor body 2 is formed to have an outer diameter dimension of φ2.2 mm and a thickness dimension of 0.20 mm; the holding body 3 is formed to have an outer diameter dimension of φ2.2 mm and a thickness dimension of 0.35 mm; the contact force transmission body 4 is formed to have an outer diameter dimension of φ1.3 mm and a thickness dimension of 0.35 mm; and the insertion hole 4a is formed to have a dimension of φ0.4 mm. Moreover, it is desirable that the sensor body 2, the holding body 3, and the contact force transmission body 4 are formed within a range of ±20% of the respective dimensions described above.

Next, an electrical connection state of the stress-electricity conversion elements (piezo resistance elements) 5 is described with reference to FIGS. 9 and 10. FIG. 9 is a substantive and schematic explanatory diagram for explaining a wire connection relationship, and shows a connection state of the lead wires 9 on the front side and the back side of the sensor body 2. Note that, the piezo resistance elements and the wiring pattern 6 on the back side of the sensor body 2 are in a state of being viewed from the front side in a see-through manner.

The piezo resistance elements (S1-a, S1-b) on the front side and the piezo resistance elements (S1-c, S1-d) on the back side are described as typical examples. As shown in FIG. 9, the lead wire 9, which is connected to an electrode 71a (on the right side in the drawing) connected between the piezo resistance elements (S1-a) and (S1-b) on the front side, is connected to an electrode 72a (on the right side in the drawing) on the back side and is led out. In addition, the lead wire 9, which is connected to an electrode 71b (on the left side in the drawing) on the front side, is connected to an electrode 72b (on the left side in the drawing) on the back side and is led out. Besides, a voltage between these lead wires 9 is detected as an output voltage V1. Note that, the electrode 71b and the electrode 72a are insulated electrodes that are not electrically connected to the piezo resistance elements. Moreover, the piezo resistance elements (S2-a, S2-b), (S3-a, S3-b), (S4-a, S4-b), (S2-c, S2-d), (S3-c, S3-d), and (S4-c, S4-d) also have the same connection relationship.

In addition, electrodes 73a and 73b for the connection to the power supply line are formed on the front side, and similarly, electrodes 74a and 74b for the connection to the power supply line are formed on the back side. The lead wire 9 connected to the electrode 73a is connected to the electrode 74a on the back side and is led out. The lead wire 9 connected to the electrode 73b on the front side is connected to the electrode 74b on the back side and is led out. Besides, a power supply E is connected between the lead wires 9. Moreover, the electrodes 73a and 74a are connected to the outer wiring pattern 62, and the electrodes 73b and 74b are connected to the inner wiring pattern 61.

As shown in FIG. 10, a bridge circuit (full bridge circuit) is configured by four elements, namely the piezo resistance elements (S1-a, S1-b) and (S1-c, S1-d), and the output voltage V1 is detected. Similarly, a full bridge circuit is configured by four elements, namely the piezo resistance elements (S2-a, S2-b) and (S2-c, S2-d), and an output voltage V2 is detected; a full bridge circuit is configured by four elements, namely the piezo resistance elements (S3-a, S3-b) and (S3-c, S3-d), and an output voltage V3 is detected; and a full bridge circuit is configured by four elements, namely the piezo resistance elements (S4-a, S4-b) and (S4-c, S4-d), and an output voltage V4 is detected. These four full bridge circuits are connected in parallel. The output voltage is output accompanying the application of a strain to the piezo resistance elements, and the output voltage is transmitted to the controller for arithmetic processing.

As described above, a full bridge circuit is configured by a total of four stress-electricity conversion elements 5, two stress-electricity conversion elements 5 being respectively formed at positions facing each other on both the front side surface and the back side surface of one spoke portion 23.

Subsequently, a method of ablation treatment using the catheter 10 is described. In the ablation treatment, an abnormal portion of the heart is identified in advance by mapping, and then the abnormal portion of an inner wall tissue of the heart is cauterized to cause coagulative necrosis.

In cauterization of the abnormal portion by the catheter 10, the catheter 10 is inserted mainly from the femoral vein or the femoral artery at the groin, and the front end of the catheter 10 is made to reach the inside of the heart while being seen through by roentgenography. Then, the control handle 11 is operated to bring the front-end electrode 14 of the catheter 10 into contact with the abnormal portion of the inner wall tissue of the heart, and a high-frequency current of, for example, 13.56 MHz, is made to flow between the front-end electrode 14 and a counter electrode plate located on the back of the patient from the high-frequency generator to cauterize the abnormal portion.

In this case, because the contact force sensor 1 is arranged in the catheter 10, a contact force (stress) of the front-end electrode 14 which is brought into contact with the inner wall tissue of the heart can be detected. Specifically, the stress-electricity conversion element (piezo resistance element) 5 formed in the contact force sensor 1 reacts to a minute strain, and the electric resistance changes because a strain is applied.

When a contact force is applied to the front-end electrode 14, the contact force is directly transmitted to the stress-electricity conversion element (piezo resistance element) 5 via the contact force transmission body 4 and the spoke portion 23. Then, the stress-electricity conversion element (piezo resistance element) 5 senses the strain of compression/expansion three-dimensionally.

For example, in a case where a stress is applied to the spoke portion 23 from a direction, a resistance value decreases when the piezo resistance element is compressed, and increases when the piezo resistance element is expanded.

Thus, the contact force can be measured by detecting, by the controller, a three-dimensional differential output due to the output voltages V1, V2, V3 and V4 generated by the bridge circuit shown in FIG. 10. By measuring the contact force in this way, the application to the medical treatment of ablation treatment becomes possible.

As described above, according to the configuration of the embodiment, a contact force sensor which has high accuracy and sensitivity and is capable of ensuring strength can be realized.

Note that, the insertion hole 4a is formed in the contact force transmission body 4, and physical quantity sensors such as a temperature sensor, a pressure sensor, and the like may be arranged at an inner wall of the insertion hole 4a. Accordingly, physical quantities such as temperature, pressure, and the like can be detected in addition to the contact force. Furthermore, a flow path member for sending out the fluid conveyed from the irrigation tube 16 may be inserted into the insertion hole 4a. Thus, the utilization of the insertion hole 4a formed in the contact force transmission body 4 is not particularly limited, and the insertion hole 4a can be appropriately and effectively functioned.

Furthermore, for example, it is preferable to arrange the contact force transmission body in the above embodiment, but it is not always necessary. The contact force may be directly sensed by the sensor body.

In addition, the contact force sensor described above is suitably used in devices such as an ablation catheter, a guiding catheter, and the like which are medical instruments, but the present invention is not limited hereto. The present invention may be applied not only in the field of medical instruments, but also to various devices which are provided with a contact force sensor and required to be miniaturized. The device to which the contact force sensor is specifically applied is not limited.

The present invention is not limited to the configuration of the above embodiment, and various modifications can be made without departing from the gist of the invention. In addition, the above embodiment is presented as an example, and is not intended to limit the scope of the invention. These new embodiments can be implemented in various other forms, and various omissions, replacements, and modifications can be performed. These embodiments and modifications thereof are included in the scope and gist of the invention, as well as included in the inventions described in the claims and the equivalent scope thereof.

What is claimed is:

1. A contact force sensor comprising a sensor body manufactured by processing a semiconductor material, wherein
the sensor body is provided with: a ring-shaped portion; a central portion formed substantially in a center of the ring-shaped portion; a spoke portion coupled to the ring-shaped portion from the central portion toward outside; and stress-electricity conversion elements which are disposed at positions facing each other on a front side and a back side of the spoke portion, and convert displacement of the spoke portion into an electric signal;
wherein the sensor body has a through hole which is formed from one surface side toward the other surface side and through which a lead wire electrically connected to the stress-electricity conversion elements passes, and an insulation layer is formed on an inner wall of the through hole;
wherein the lead wire is introduced in a way of passing through the through hole, and is joined to an electrode layer around the through hole on the front side and the back side via a brazing material, thereby forming a gap between the lead wire and an inner wall of the through hole.

2. The contact force sensor according to claim 1, wherein two stress-electricity conversion elements are formed on each of the front side and the back side of the spoke portion.

3. The contact force sensor according to claim 2, wherein the stress-electricity conversion elements are arranged on a center side and an outer periphery side of the spoke portion.

4. The contact force sensor according to claim 1, wherein electrodes are formed in a circumferential direction on two sides of the stress-electricity conversion elements disposed in the spoke portion.

5. The contact force sensor according to claim 1, wherein a plurality of the spoke portions are formed.

6. The contact force sensor according to claim 1, wherein a wiring pattern configured to connect a plurality of the stress-electricity conversion elements in common is formed in the sensor body.

7. The contact force sensor according to claim 1, wherein an opening is formed in the central portion of the sensor body.

8. The contact force sensor according to claim 1, comprising a holding body that holds the sensor body.

9. The contact force sensor according to claim 1, wherein a contact force transmission body is arranged on the sensor body.

10. The contact force sensor according to claim 9, wherein an insertion hole is formed in the contact force transmission body.

11. The contact force sensor according to claim 1, wherein the stress-electricity conversion elements are bridge-connected, thereby constituting a bridge circuit.

12. The contact force sensor according to claim 1, wherein a conductor core wire portion, which is obtained in a way that an insulation coating is removed from the lead wire electrically connected to the stress-electricity conversion elements, passes through the through hole.

13. The contact force sensor according to claim 12, wherein a front end of the conductor core wire portion passing through the through hole has a linear shape.

14. The contact force sensor according to claim 12, wherein a conductor core wire in the lead wire is formed by a copper-silver alloy wire.

15. The contact force sensor according to claim 1, wherein the lead wire electrically connected to the stress-electricity conversion elements is connected by an electrode made of a brazing material.

16. The contact force sensor according to claim 15, wherein the electrode is a metal having a low melting point.

17. The contact force sensor according to claim 15, wherein the electrode enters inside of the through hole, thereby forming an intrusion portion.

18. The contact force sensor according to claim 1, wherein the electrode layer is formed around the through hole and extends toward an inner wall side of the through hole.

19. The contact force sensor according to claim 1, wherein an insulation coating is formed on an outer surface of the sensor body.

20. The contact force sensor according to claim 19, wherein the insulation coating has flexibility.

21. The contact force sensor according to claim 19, wherein a material having biocompatibility is used for the insulation coating.

22. A device provided with a contact force sensor, comprising the contact force sensor according to claim 1.

* * * * *